US005962330A

United States Patent [19]

Frederico et al.

[11] Patent Number: 5,962,330
[45] Date of Patent: Oct. 5, 1999

[54] METHOD FOR DETECTING ACID- AND BASE-EXTRACTABLE MARKERS

[75] Inventors: Justin J. Frederico, Paterson; Haresh A. Doshi, Somerville, both of N.J.

[73] Assignee: Morton International, Inc., Chicago, Ill.

[21] Appl. No.: 08/884,156

[22] Filed: Jun. 27, 1997

[51] Int. Cl.$^6$ ........................................ G01N 33/32
[52] U.S. Cl. ................ 436/56; 436/132; 436/139; 436/163; 436/164; 436/169
[58] Field of Search ............... 436/56, 163, 164, 436/169, 139, 132; 44/903

[56] References Cited

U.S. PATENT DOCUMENTS

| | | |
|---|---|---|
| 4,209,302 | 6/1980 | Orelup . |
| 4,904,765 | 2/1990 | Derber et al. . |
| 4,918,020 | 4/1990 | Nowak . |
| 5,205,840 | 4/1993 | Friswell et al. . |
| 5,244,808 | 9/1993 | Nowak . |
| 5,252,106 | 10/1993 | Hallisy . |
| 5,304,493 | 4/1994 | Nowak . |
| 5,358,873 | 10/1994 | Nowak . |
| 5,387,525 | 2/1995 | Munkholm . |
| 5,490,872 | 2/1996 | Friswell et al. . |

OTHER PUBLICATIONS

Webster's Ninth New Collegiate Dictionary, Merriam–Webster (1987) pp. 239, 347 and 476, 1987.

*Primary Examiner*—Jan Ludlow
*Attorney, Agent, or Firm*—Wayne E. Nacker; Gerald K. White

[57] ABSTRACT

Markers which are soluble in petroleum fuel and are extractable from petroleum fuel by either acidic aqueous solutions or basic solutions and develop a color in the presence of the extracting acidic or basic aqueous solution, are identified by passing a specimen putatively containing the marker through an acidic resin column or a basic resin column, as the case may be.

6 Claims, No Drawings

METHOD FOR DETECTING ACID- AND BASE-EXTRACTABLE MARKERS

The present invention is directed to a method of detecting markers in liquids, particularly hydrophobic liquids and most particularly petroleum fuels and the like.

BACKGROUND OF THE INVENTION

It is well known to tag petroleum fuels with "silent" markers so that the fuels can be identified for tax purposes, source of manufacture, brand identification and dilution or adulteration. Such markers are added to the fuels at low levels, typically at levels of 100 ppm or below, where they are not readily detectable with the naked eye. However, as it is necessary to be able to easily detect the presence of such markers, a simple chemical test must be available for their detection.

Generally the chemical test involves an extraction with either an acidic aqueous medium or an alkaline aqueous medium accompanied by reaction with a chromophore-producing reagent. As such, markers used to tag petroleum fuels must be readily miscible with the hydrophobic fuel, but in the presence of either hydrogen ion or hydroxyl ion become highly preferentially soluble in the respective aqueous medium. The chromophore-producing reactant may be the acid itself, such as with the markers described in U.S. Pat. No. 5,490,872, the teachings of which are incorporated herein by reference; the base itself, such as with the markers described in U.S. Pat. No. 5,205,840, the teachings of which are incorporated herein by reference, or an additional agent, such is the case with the markers described in U.S. Pat. No. 4,209,302 where the marker is reacted with a diazo compound contemporaneously with or subsequent to extraction with an acidic aqueous medium. The present invention is particularly directed to those dyes which are extractable with an acid or a base and in which the acid or base develops the color in the marker.

Extractions, particularly in the field, involve liquids that can leak or spill. Furthermore, liquids present a disposal problem. In order to ensure a complete separation of the petroleum and aqueous phase, it is conventional to include surfactants in the extraction solution. As a result, the sampled petroleum fuel is contaminated and cannot be returned to its source. Accordingly, the entire extraction mixture, including both the aqueous phase and the petroleum fuel phase must be stored and transported for subsequent proper disposal. Furthermore, separation of immiscible layers into clear, homogeneous phases may be relatively slow, depending on the specific components of the aqueous/non-aqueous system, taking from 5 to 15 min., which typically results in "dead time" for the tester. The volume of liquid needed for extraction can be large due to low concentration of the marker. Also, concentration of dilute marker by evaporating liquid is time-consuming.

Because of the inconvenience of liquid extractions, resin column testing for markers have been proposed. U.S. Pat. No. 5,304,493 describes extracting a fuel specimen tagged with an anthraquinone dye in a column of unbonded silica followed by eluting the dye with a solvent, such as toluene or dichloromethane. Like extraction, however, this method can be time-consuming and produces waste solvents which must be disposed of. U.S. Pat. No. 5,244,808 describes a three-resin column test for detecting markers of the type described in above-referenced U.S. Pat. No. 4,209,302.

The present invention is directed to a quick, simple test for the identification of petroleum fuel markers which minimizes disposal problems and is non-destructive of the specimen being sampled.

SUMMARY OF THE INVENTION

In accordance with the invention, a petroleum fuel marker which is either acid-extractable and undergoes a chromophoric reaction in the presence of acid, or is base-extractable and undergoes a chromophoric reaction in the presence of base, is identified substantially instantaneously by drawing a specimen of the fuel through an ion-exchange resin column which is acidic or basic, as the case may be. As the column adds nothing to the sample being tested, the tested sample may be reintroduced to the bulk of material being tested.

DETAILED DESCRIPTION OF CERTAIN PREFERRED EMBODIMENTS

Although the markers described herein are described as "petroleum fuels markers", e.g., for marking kerosene, gasoline, diesel or the like, the method of the present invention is applicable to any organic liquid which might be tagged with markers for subsequent identification. Typically, such a liquid, like petroleum fuels, would be water-immiscible; however, the method of the present invention is also suitable for identifying markers in water-miscible solvents, such as ethanol, as is used, for example, in Brazil as an automotive fuel. Commonly tagged organic liquids include diesel fuel, kerosene, isooctane, gasoline, and refrigerant oil.

The invention is generally directed to markers which are extractable from non-polar solvents into acidic or alkaline aqueous solutions and develop a color in the presence the acid or base, respectively. In addition to the markers described in above-referenced U.S. Pat. No. 5,490,872, additional examples of acid-extractable markers are found in U.S. Pat. No. 4,904,765, the teachings of which are incorporated herein by reference. In addition to the markers described in above-referenced U.S. Pat. No. 5,205,840, additional examples of alkaline-extractable markers are found in U.S. Pat. No. 5,252,106, the teachings of which are incorporated herein by reference.

Suitable resins for detecting acid-extractable markers include, but are not limited to, polystyrene sulfonic acid cation exchange resin in the $H^+$ form resin; acidic alumina; formic or hydrochloric acid impregnated silica; and mixtures thereof. A suitable resin for detecting alkaline-extractable markers is a polystyrene anion exchange resin bearing an amine-functional group in the $NH_2$ form.

Small, pre-packed resin cartridges suitable for the tests of the present invention are available, e.g., sold as Maxi-Clean™ IC-H and IC-H Plus Cartridges by Alltech Associates, Inc., Deerfield, Ill. Such cartridges have heretofore been sold for the purpose of eliminating matrix interference from samples prior to analysis by ion chromatography. Such cartridges may typically contain only a small amount of material, meaning that only a very small volume of specimen need be tested. With commercially available cartridges, samples as small as 3 ml. may be tested, and even smaller columns could be conceivably be employed. The sample may be drawn into the column merely by use of a syringe, and the sample may be subsequently evacuated from the column, by positive pressure applied to the same syringe. As the column does not affect the specimen other than remove the marker, the specimen may be returned to its source without fear of contamination.

Again, color development is substantially instantaneous, developing as the specimen is drawn into the column. The color is apparent even with the specimen in the column and remains when the specimen is expelled from the column. The method provides a quick qualitative test for the presence of a marker, and by comparison with a color chart, provides a rough quantitative test. The cartridge may be manufactured as a substantially sealed part, and discarding of the used cartridge and syringe present substantially no disposal problems.

Detection by the naked eye of the color produced by materials tagged with as low as 10 ppm (parts per million by weight) is possible.

The mechanical form which the column takes is not significant, and the column could be packed, for example, directly in a syringe. In the case of hazardous materials which may be tagged, identification is carried out with substantially no exposure to the tester.

The invention will now be described in greater detail by way of specific examples.

EXAMPLE 1

A syringe was fitted with a 0.5 ml. bed volume cartridge packed with a polystyrene sulfonic acid cation exchange resin in the $H^+$ form. 3 ml. of kerosene marked with 20 ppm Mortrace® AB, an acid extractable marker of the type described in U.S. Pat. No. 5,490,872, was drawn into the syringe barrel via the cartridge. The packing changed color to red. The barrel was depressed and the solvent returned. The cartridge was compared to a chart to correlate it to concentration levels of Mortrace® AB.

EXAMPLE 2

A syringe was fitted with a cartridge packed with a polystyrene anion exchange resin bearing an amine-functional group in the $NH_2$ form. 3 ml. of kerosene marked with 20 ppm Mortrace® SB a dye of the type described in U.S. Pat. No. 5,205,840 was drawn into the syringe barrel via thee cartridge. The packing changed color to purple-blue. The barrel was depressed and the kerosene returned. The cartridge was compared to a chart to match it to Mortrace® SB.

What is claimed is:

1. A method of identifying a petroleum fuel-miscible marker which is either
   a) extractable from a petroleum fuel in acidic aqueous solution and undergoes a chromophoric reaction in the presence of acid which produces a visible color, or
   b) extractable from a petroleum fuel in alkaline aqueous solution and undergoes a chromophoric reaction in the presence of base which produces a visible color, the method consisting of the steps of:
      withdrawing an organic liquid specimen which putatively contains said marker,
      passing said liquid specimen through a resin column which in the case of a) is an acidic ion exchange resin and in the case of b) is a basic ion exchange resin, and
      noting visible color in said column resulting from, in the case of a) said chromophoric reaction which takes place in the presence of an acid, and in the case of b) said chromophoric reaction which takes place in the presence of a base.

2. The method of claim 1 wherein said marker is extractable by acidic aqueous solution.

3. The method of claim 2 wherein said resin column is packed with material selected from the group consisting of polystyrene sulfonic acid cation exchange resin in the $H^+$ form resin; acidic alumina; formic or hydrochloric acid impregnated silica; and mixtures thereof.

4. The method of claim 2 wherein said resin column is packed with polystyrene sulfonic acid cation exchange resin in the $H^+$ form resin.

5. The method of claim 1 wherein said marker is extractable by alkaline aqueous solution.

6. The method of claim 4 wherein said resin column is packed with a polystyrene anion exchange resin bearing an amine-functional group in the $NH_2$ form.

* * * * *